(12) United States Patent
Marksteiner

(10) Patent No.: US 6,597,945 B2
(45) Date of Patent: Jul. 22, 2003

(54) METHOD FOR DETECTING LIVING HUMAN SKIN

(75) Inventor: Stephan Marksteiner, München (DE)

(73) Assignee: Infineon Technologies AG, Munich (DE)

( * ) Notice: Subject to any disclaimer, the term of this patent is extended or adjusted under 35 U.S.C. 154(b) by 101 days.

(21) Appl. No.: 09/757,329

(22) Filed: Jan. 9, 2001

(65) Prior Publication Data

US 2001/0005424 A1 Jun. 28, 2001

Related U.S. Application Data

(63) Continuation of application No. PCT/DE99/01974, filed on Jul. 1, 1999.

(30) Foreign Application Priority Data

Jul. 9, 1998 (DE) .......................................... 198 30 830

(51) Int. Cl.$^7$ ................................................. A61B 5/05
(52) U.S. Cl. ..................................................... 600/547
(58) Field of Search ................................. 600/547, 300; 341/126, 155

(56) References Cited

U.S. PATENT DOCUMENTS 5,382,956 A * 1/1995 Baumgartner et al. ...... 341/126

FOREIGN PATENT DOCUMENTS

| DE | 91 07 918.7 U1 | 1/1992 |
|----|----|----|
| DE | 197 40 523 A1 | 3/1999 |

OTHER PUBLICATIONS

International Publication WO 98/35118 (Schelter), dated Aug. 13, 1998.
Yoshitake Yamamoto et al.: "Measurement of electrical bio–impedance and its applications", Medical Progress through Technology, Dordrecht, Netherlands, vol. 12, 1987, Nos. 3–4, pp. 171–183, XP–002122046.
International Publication WO 95/26013 (Osten et al.) dated Sep. 28, 1995.
International Publication WO 95/14111 (Kallo et al.), dated Apr. 1, 1997.

* cited by examiner

Primary Examiner—Max F. Hindenburg
Assistant Examiner—Brian Szmal
(74) Attorney, Agent, or Firm—Laurence A. Greenberg; Werner H. Stemer; Ralph E. Locher

(57) ABSTRACT

A characteristic curve of the impedance of a skin surface is measured as a function of the frequency of an electric AC voltage by applying the voltage to at least one electric conductor which is galvanically or capacitively coupled to the skin surface. The characteristic curve is compared with a reference characteristic curve, which has been generated previously. If the characteristic curve substantially corresponds to the reference characteristic curve, the skin surface is recognized as belonging to living tissue.

3 Claims, 2 Drawing Sheets

METHOD FOR DETECTING LIVING HUMAN SKIN

CROSS-REFERENCE TO RELATED APPLICATION

This application is a continuation of copending International Application No. PCT/DE99/01974, filed Jul. 1, 1999, which designated the United States.

BACKGROUND OF THE INVENTION

Field of the Invention

The invention relates to a method for detecting living human skin.

Modern access authorization systems may, inter alia, use fingerprints for identification purposes. An essential precondition for such an identification is that it must be protected against forgery or manipulation. In particular, it must be ensured that it is not possible to obtain access authorization with fake fingers or cut-off fingers. It is therefore essential also to check, together with the fingerprint, that the person with this fingerprint is alive.

Various methods for an electronic identification of persons are described in International Publication No. WO 95/26013. In addition to recording a fingerprint, these methods can determine whether the person is alive. These methods include recording the pulse frequency or electrocardiographic signals, measuring the oxygen content of the blood, the skin temperature, the blood pressure or mechanical properties of the skin surface.

SUMMARY OF THE INVENTION

It is accordingly an object of the invention to provide a method for detecting living human skin which is simple and which is suitable, in particular, for use in conjunction with a fingerprint sensor.

With the foregoing and other objects in view there is provided, in accordance with the invention, a method for detecting living human skin, the method includes the steps of:

providing a region of a skin surface close to at least one electric conductor by bringing the region of the skin surface in contact with the at least one electric conductor or by providing the region of the skin surface at a given distance from the at least one electric conductor;

applying an electric potential of a superimposition of frequencies or an electric AC voltage with a variable frequency to the at least one electric conductor;

determining, with a measurement carried out with the electric potential or the electric AC voltage, an electric impedance as a specific function of time and/or frequency, by determining a real part and an imaginary part of the electric impedance or by determining a frequency and an absolute value of the electric impedance; and checking whether the specific function corresponds to a reference function.

According to another mode of the invention, the electric potential is provided as a superimposition of frequencies, wherein the superimposition results in a voltage pulse or a voltage jump.

According to yet another mode of the invention, the electric potential is provided by superimposing the frequencies of a limited interval.

According to a further mode of the invention, the region of the skin surface is provided close to at least two electric conductors by bringing the region of the skin surface in contact with the at least two electric conductors or by providing the region of the skin surface at a given distance from the at least two electric conductors. The at least two electric conductors are electrically insulated from one another and are spaced by a distance of at least 2 mm from one another.

Other features which are considered as characteristic for the invention are set forth in the appended claims.

Although the invention is illustrated and described herein as embodied in a method for detecting living human skin, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Referring now to the figures of the drawings, the invention is described in detail. The method according to the invention utilizes the fact that living human skin has a characteristic layer structure. It is of great importance for the invention described here that these layers of the skin have clearly different electric conductivities. If these layers are located in the electric field of a configuration or assembly of electrodes, a resistive/capacitive system with a very characteristic frequency curve of frequency variation is formed.

FIGS. 1–4 are diagrams in which the ohmic resistance (real part of the impedance) and the capacitance (proportional to the imaginary part of the impedance) are plotted for various conditions against the logarithm of the frequency of the applied voltage. In the basic measurement, an index finger was applied to (i.e. positioned on) a silicon wafer covered with oxide, and the impedance of this configuration was measured.

Figure 1:
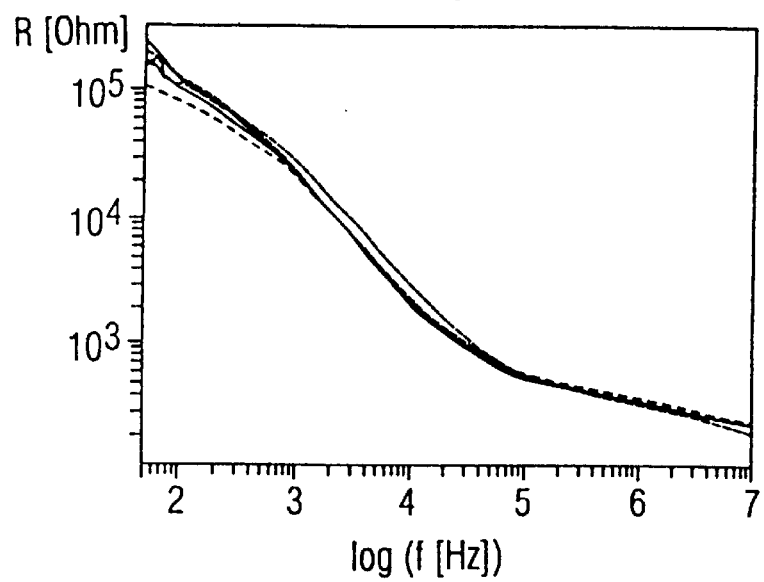
FIGS. 1 and 2 are graphs of ohmic resistances plotted against the logarithm of a frequency of an applied voltage.
Figure 3:
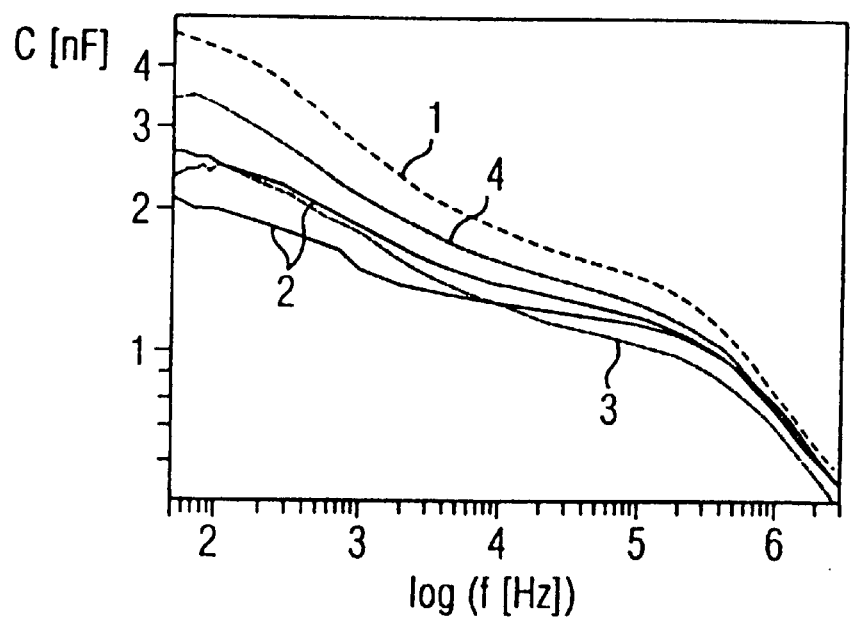
FIGS. 3 and 4 are graphs of capacitances plotted against the logarithm of a frequency of an applied voltage.

Families of curves for various finger states or finger conditions are plotted respectively in the graphs of FIGS. 1 and 3. The dashed curve 1 refers to a wet finger, the continuous curve 2 to a normal finger, and the lower dotted curve 3 to a dry finger. The upper dotted curve 4 is based on the measurement of the tip of a middle finger.

Figure 2:
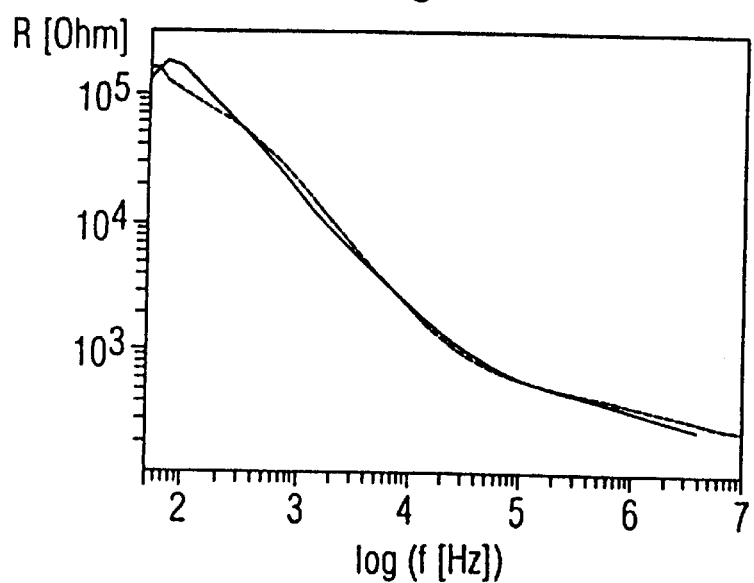
Figure 4:
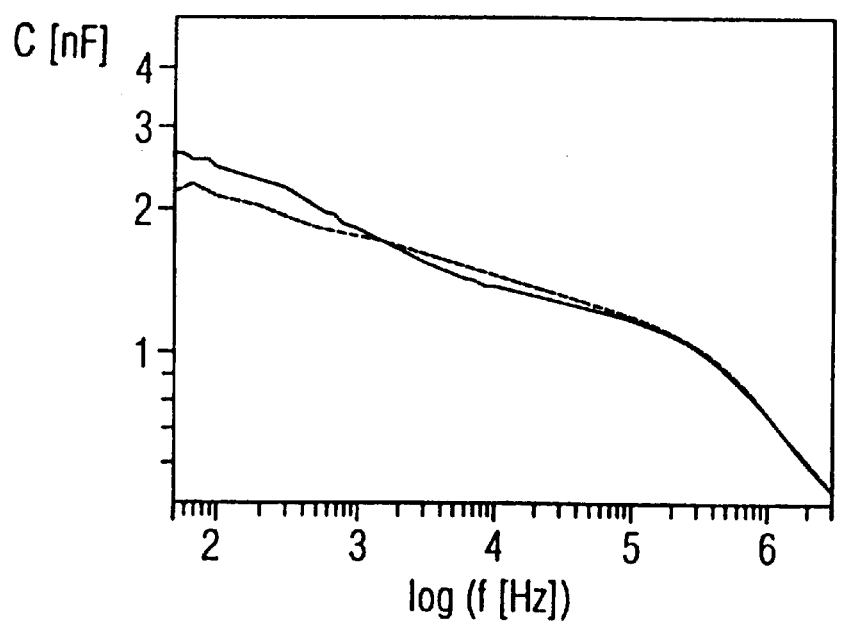

Characteristic curves for two different test persons are illustrated in the graphs shown in FIGS. 2 and 4. It is easy to see that the same characteristic curve shape of these curves results in a fashion that is largely independent of the finger state and of the test person.

The characteristic of the curve shape of the ohmic resistance is particularly pronounced. This characteristic curve shape can be faked or simulated only with difficulty when using an artificial finger. In the case of a cut-off finger the curve shape changes rapidly as a result of the skin tissue dying off. In the following it is described how this characteristic impedance curve shape can be used to verify the authenticity and living nature of the finger applied.

To start, a reference characteristic curve is generated in a first step. In this case, it is possible both to measure the frequency course directly, as illustrated in the figures, or else also to use the temporal course of a measured signal. An example of the latter method is the application of a voltage jump to the electrodes and the measurement of the temporal course or variation in the charging current. The respective characteristic curves look entirely different, but are equivalent in principle, since they are correlated with one another via a Fourier transformation or a convolution. The method used depends on the respective application. If high requirements are placed on the reliability of the identification, it is possible, for example, to evaluate the real and imaginary parts of the impedance characteristic. In the case of simpler applications, it suffices to use the absolute value of the impedance, since this absolute value can be obtained by a simple averaging of the measurement current. The reference characteristic curve is preferably generated such that it represents an average course for the impedance curve. This can be achieved, for example, by averaging over a plurality of curves, possibly recorded under different conditions. The reference characteristic curve is preferably recorded separately for each person to be identified later.

The selected impedance values in the selected range of the AC voltage frequency are stored, for example, together with the essential characteristics (minutiae) of the fingerprint. It is then possible, when checking the fingerprint, to compare both the fingerprint itself and the characteristic curve for the purpose of detecting life with the stored values. Since only slight fluctuations are to be established between different persons (see FIGS. 2 and 4), it is possible, if appropriate, also to use a single reference curve for all persons to be identified. However, when comparing a current or actual characteristic curve with this stored reference characteristic curve it is then necessary to permit somewhat larger fluctuation ranges i.e. wider tolerance limits.

Instead of using a pure sinusoidal oscillation for the purpose of measuring the frequency dependence, it is also possible to use a superimposition of frequencies. Such superimpositions, for example pulse shapes (square-wave pulses, sawtooth pulses or the like), are often easier to generate than pure sinusoidal oscillations. The region in which the superimposed frequencies are situated can be restricted to a specific interval width by suitable filtering. The measured values or characteristics curves obtained correspond to an averaging of measured values with a sinusoidal excitation. If the interval width of the superimposed frequencies is chosen to be sufficiently small, however, it is also possible to use this simplified method to generate a satisfactory characteristic curve, or to record it during the current measurement.

With each identification of a person, the relevant characteristic curve is measured and compared with the reference characteristic curve. If there is a satisfactory correspondence in this case, and the person-specific measured values (minutiae of the fingerprint) likewise correspond to the reference values, the person is considered to have been identified and receives the access authorization. Such a comparison of characteristic curves can be performed in a way known per se by evaluating the difference between the function values. It is possible, for example, to sum or integrate the squares of the difference between the values of the characteristic curves at each frequency, to sum or integrate the absolute values of these differences, or to determine the maximum of these differences. The accuracy of the comparison can also be raised, if appropriate, by comparing the logarithms or the first derivatives of the characteristic curves with one another.

The method according to the invention can be carried out in the case of a fingerprint sensor by using electric conductors in the sensor. Use is made for this purpose of a sensor in which, in or below a bearing surface or touch surface for recording a fingerprint, electric conductors are fitted which, upon application of the fingertip, come into direct contact with the skin surface (galvanic coupling) or have a specific distance from the skin surface (capacitive coupling). In the latter case, a dielectric layer is located, as protective layer or covering, between the conductor and the bearing surface for the finger, for example.

For measuring purposes, it is possible to use a single conductor or two conductors electrically insulated from one another. If only one conductor is used, the finger applied acts as a connection to the grounding potential. In the case of the use of two electric conductors, the conductors are preferably provided at a distance which is greater than the thickness of the epidermis. The method can therefore be carried out using conductors which are at a distance of at least 2 mm from one another. It is sufficient if the conductors are two metal plates with approximate dimensions of 10 $mm^2$. Depending on the desired measuring resolution, it is also possible to employ substantially smaller dimensions. The impedance can be measured in a way known per se. It is merely necessary to ensure that the selected measuring method supplies a result which is sufficiently accurate for the purpose. If the method is used in the case of a fingerprint sensor, the conductor or the conductors for detecting life is or are preferably provided at the edge of the bearing surface for the fingertip. However, since, as a rule, the sensor itself is constructed from electrically conductive sensor elements, individual ones of these sensor elements can also be used to carry out the method described. The method can therefore also be carried out in principle with conventional sensors by using suitable electronic devices.

I claim:

1. A method for detecting life from human skin, the method which comprises:

one of contacting a region of a skin surface with at least one electric conductor and applying the region of the skin surface to a bearing surface or touch surface at a distance from the at least one electric conductor;

applying an electric potential of one of a superimposition of frequencies having one of a voltage pulse and a voltage jump and an electric AC voltage with a variable frequency varied over a selected range to the at least one electric conductor;

determining, with a measurement carried out with the electric potential, a real part and an imaginary part of or an absolute value of an electric impedance as a function of one of time and frequency; and checking if the determined function corresponds to a reference function.

2. The method according to claim 1, which comprises providing the electric potential by superimposing the frequencies from a limited interval.

3. The method according to claim 1, wherein the at least one electric conductor are at least two electric conductors, and which comprises:

one of contacting the region of the skin surface with the at least two electric conductors and bringing the region of the skin surface to the given distance from the at least two electric conductors; and electrically insulating the at least two electric conductors from one another and spacing the at least two electric conductors by at least 2 mm from one another.

* * * * *